(12) United States Patent
Haramoto

(10) Patent No.: US 7,390,433 B2
(45) Date of Patent: Jun. 24, 2008

(54) BENZENE DERIVATIVE HAVING LONG, LINEAR CONJUGATED STRUCTURE, PROCESS FOR PRODUCING BENZENE DERIVATIVE, AND LIQUID-CRYSTAL MATERIAL

(75) Inventor: Yuichiro Haramoto, Kofu (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 0 days.

(21) Appl. No.: 10/548,385

(22) PCT Filed: Mar. 22, 2004

(86) PCT No.: PCT/JP2004/003824

§ 371 (c)(1),
(2), (4) Date: Jun. 16, 2006

(87) PCT Pub. No.: WO2004/085398

PCT Pub. Date: Oct. 7, 2004

(65) Prior Publication Data

US 2007/0029520 A1    Feb. 8, 2007

(30) Foreign Application Priority Data

Mar. 24, 2003  (JP) ............................. 2003-079624

(51) Int. Cl.
*C09K 19/52* (2006.01)
*C09K 19/58* (2006.01)
*C07D 211/82* (2006.01)

(52) U.S. Cl. ............................ 252/299.01; 252/299.02; 546/339

(58) Field of Classification Search .................. 546/339; 349/2; 252/299.01, 299.02
See application file for complete search history.

(56) References Cited

FOREIGN PATENT DOCUMENTS

JP    3-220243    9/1991

OTHER PUBLICATIONS

Monolayers and LB Films of Highly Polarizable Oligo (phenylenevinylene) Derivatives, pp. 905-908, 1991, Watabe et. al.*
A. Watakabe et al.; "Monolayers and LB Films of Highly Polarizable Oligo (phenylenevinylene), Derivatives", Chemistry Letters, 1991, No. 6, pp. 905-908.

* cited by examiner

Primary Examiner—Janet L. Andres
Assistant Examiner—Binta Robinson
(74) Attorney, Agent, or Firm—Westerman, Hattori, Daniels & Adrian, LLP.

(57) ABSTRACT

The present invention provides, in a method for transporting charge using the molecular orientation in a liquid-crystalline state, a novel benzene derivative having a long, linear conjugated structure expected to have satisfactory charge-transport properties without photoexcitation, a process for producing the benzene derivative, and a liquid-crystal material including the benzene derivative. The benzene derivative having a long, linear conjugated structure is represented by general formula (1):

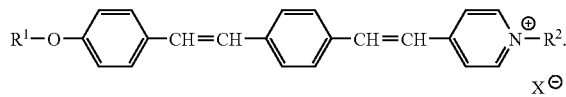

(1)

3 Claims, No Drawings

BENZENE DERIVATIVE HAVING LONG, LINEAR CONJUGATED STRUCTURE, PROCESS FOR PRODUCING BENZENE DERIVATIVE, AND LIQUID-CRYSTAL MATERIAL

TECHNICAL FIELD

The present invention relates to a novel benzene derivative having a long, linear conjugated structure, the benzene derivative being useful as a charge-transport material used in, for example, optical sensors, organic electroluminescent elements (EL elements), photoconductors, spatial modulators, thin-film transistors, charge-transport substances for electrophotographic photoreceptors, photolithographic materials, solar cells, nonlinear optical materials, organic semiconductor capacitors, or other sensors. The present invention also relates to a liquid-crystal material and a process for producing the benzene derivative.

BACKGROUND ART

In recent years, organic electroluminescent elements using organic materials as hole-transport materials or charge-transport materials constituting the electroluminescent elements have been intensively studied.

As such charge-transport materials, for example, anthracene derivatives, anthraquinoline derivatives, imidazole derivatives, styryl derivatives, hydrazone derivatives, triphenylamine compounds, poly(N-vinylcarbazoles), and oxadiazoles are known.

Liquid-crystal compounds have been used as materials for displays and applied to various devices, such as clocks, desktop electronic calculators, television sets, personal computers, and cellular phones. The liquid-crystal materials are classified into thermotropic liquid crystals (liquid crystals in which transitions depend on temperature) and lyotropic liquid crystals (liquid crystals in which transitions depend on concentration) on the basis of the mechanisms of phase transitions. From the standpoint of molecular arrangements, these liquid crystals are classified into three groups: smectic liquid crystals, nematic liquid crystals, and cholesteric liquid crystals. The liquid crystals are also known as anisotropic liquids and exhibit optical anisotropy similarly to optically uniaxial crystals. Observation using an orthoscope is usually performed between crossed Nicols, and is useful for the identification of types of liquid crystals and for the determination of the transition temperatures of liquid-crystal phases. The smectic liquid crystals are classified into A, B, C, D, E, F, and G on the basis of characteristic birefringent optical patterns observed with the orthoscope.

Hanna et al. have found that liquid-crystal compounds having smectic phases are capable of transporting charges and have proposed charge-transport materials using the liquid crystal compounds. They have proposed, for example, a liquid-crystalline charge-transport material exhibiting smectic liquid crystallinity and having a reduction potential of −0.3 to −0.6 (V vs. SEC) with reference to a standard calomel electrode (SEC) (Japanese Unexamined Patent Application Publication No. 09-316442); a liquid-crystalline charge-transport material including a liquid crystalline compound exhibiting a smectic phase having self-orientation properties and a predetermined amount of fullerene C70 having a sensitizing effect (Japanese Unexamined Patent Application Publication No. 11-162648); a polymer membrane in which a liquid-crystalline charge-transport material is dispersed in the polymer matrix, in other words, a polymer membrane in which a liquid-crystalline compound exhibiting a smectic phase is dispersed (Japanese Unexamined Patent Application Publication No. 11-172118); a liquid-crystalline charge-transport material including a mixture containing a smectic liquid-crystalline compound (Japanese Unexamined Patent Application Publication No. 11-199871); a liquid-crystalline charge-transport material having smectic liquid crystallinity and having an electron mobility or hole mobility of $1 \times 10^{-5}$ $cm^2/v \cdot s$ or more (Japanese Unexamined Patent Application Publication No. 10-312711); and a liquid-crystalline charge-transport material including a smectic liquid crystalline compound having, in one molecule, a functional group capable of forming a new intermolecular or intramolecular bond and a functional group capable of transporting a hole and/or electron (Japanese Unexamined Patent Application Publication No. 11-209761).

Smectic liquid-crystalline compounds disclosed in the above-described Patent Documents include smectic liquid-crystalline compounds each having a 6-π-electron aromatic ring such as a benzene ring, a pyridine ring, a pyrimidine ring, a pyridazine ring, a pyrazine ring, or a tropolone ring; smectic liquid-crystalline compounds each having a 10-π-electron aromatic ring such as a naphthalene ring, azulene ring, a benzofuran ring, an indole ring, an indazole ring, a benzothiazole ring, a benzoxazole ring, a benzimidazole ring, a quinoline ring, an isoquinoline ring, a quinazoline ring, or a quinoxaline ring; and smectic liquid-crystalline compounds each having a 14-π-electron aromatic ring such as a phenanthrene ring, or an anthracene ring. In these compounds, charges are transported in a smectic-A phase. However, the above-described method for transporting charges requires photoexcitation. Furthermore, conductivity is $10^{-13}$ s/cm without photoexcitation and $10^{-11}$ s/cm in a photoexcited state. The conductivity values are the same levels as those of an insulating material.

DISCLOSURE OF THE INVENTION

The present inventors have proposed a method for transporting charge by applying a voltage to a liquid-crystalline compound in a smectic-B phase or in a solid state due to phase transition from the smectic-B phase (Japanese Unexamined Patent Application Publication No. 2001-351786).

The present invention has been accomplished in view of such known techniques. It is an object of the present invention to provide, in a method for transporting charge using the molecular orientation in a liquid-crystalline state, a novel benzene derivative having a long, linear conjugated structure expected to have satisfactory charge-transport properties without photoexcitation, a process for producing the benzene derivative, and a liquid-crystal material including the benzene derivative.

A first aspect of the present invention provides a benzene derivative having a long, linear conjugated structure represented by general formula (1):

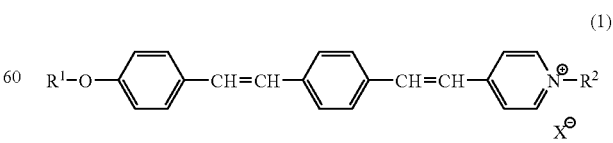

wherein $R^1$ represents a straight or branched alkyl group, an alkoxy group, or a group having an unsaturated bond represented by general formula (2):

(2)

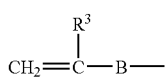

(wherein $R^3$ represents a hydrogen atom or a methyl group, and B represents an alkylene group, —CO—O—$(CH_2)n$, —$C_6H_4$—$CH_2$—, or —CO—), $R^2$ represents an alkyl group or an alkoxy group, and X represents a halogen atom.

A second aspect of the present invention provides a process for producing a benzene derivative having a long, linear conjugated structure represented by general formula (1):

(1)

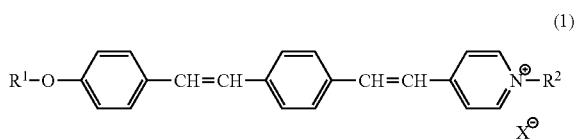

(wherein $R^1$, $R^2$, and X are the same as described above), the process including a first step of allowing a benzaldehyde derivative represented by general formula (3):

(3)

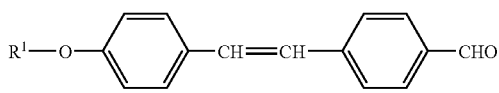

to react with a phosphonium salt represented by (4):

(4)

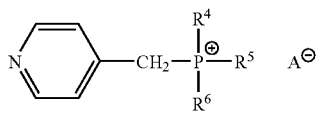

(wherein $R^4$, $R^5$, and $R^6$ are each a monovalent organic group, and A represents a halogen atom), in the presence of a base to produce a pyridine derivative represented by general formula (5):

(5)

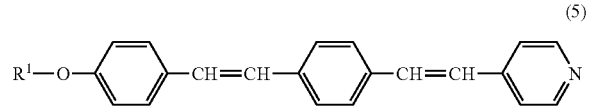

(wherein $R^1$ is the same as described above); and a second step of allowing the pyridine derivative to react with a halogenated compound represented by general formula (6):

$R^2$—X (6)

(wherein $R^2$ and X are the same as described above).

A third aspect of the present invention provides a liquid-crystal material including a benzene derivative having a long, linear conjugated structure represented by general formula (1) described above or a compound derived from the benzene derivative.

BEST MODE FOR CARRYING OUT THE INVENTION

The present invention will be described in detail below.

A novel compound provided by the present invention is a benzene derivative having a long, linear conjugated structure represented by general formula (1).

$R^1$ in the benzene derivative having a long, linear conjugated structure represented by general formula (1) represents a straight or branched alkyl group, an alkoxy group, or a group having an unsaturated bond represented by general formula (2). The alkyl group has 1 to 18 carbon atoms. Specific examples thereof include a methyl group, an ethyl group, a butyl group, a pentyl group, a hexyl group, an octyl group, a dodecyl group, pentadecyl group, and an octadecyl group. Among these, an alkyl group having 6 to 18 carbon atoms is particularly preferable. Furthermore, when the alkyl group is a branched alkyl group represented by general formula: $CH_3$—$(CH_2)_m$—$CH(CH_3)$—$(CH_2)_n$—$CH_2$— (wherein n represents 0 to 7, and m represents 0 to 7), the solubility of the benzene derivative can be improved.

The alkoxy group is represented by general formula: $C_nH_{2n+1}O$, wherein n is preferably 1 to 18 and particularly preferably 6 to 18.

$R^3$ in the group having an unsaturated bond represented by the general formula (2) represents a hydrogen atom or a methyl group. B represents an alkylene group, —CO—O—$(CH_2)n$-, —$C_6H_4$—$CH_2$—, or —CO—. The alkylene group may be straight or branched and preferably has 1 to 18 carbon atoms. Specific examples thereof include a methylene group, an ethylene group, a trimethylene group, a tetramethylene group, a pentamethylene group, an ethylethylene group, a propylene group, a butylene group, a hexylene group, an octadecylene group, a nonylene group, a decylene group, and a dodecylene group. Furthermore, n in —CO—O—$(CH_2)_n$— is particularly preferably 1 to 18.

$R^2$ in the benzene derivative having a long, linear conjugated structure represented by general formula (1) represents an alkyl group or an alkoxy group. The alkyl group has 1 to 18 carbon atoms. Specific examples thereof include a methyl group, an ethyl group, a butyl group, a pentyl group, a hexyl group, an octyl group, a dodecyl group, a pentadecyl group, and an octadecyl group. Among these, an alkyl group having 1 to 8 carbon atoms is particularly preferred. The alkoxy group is represented by general formula: $C_nH_{2n+1}O$, wherein n is preferably 1 to 20 and particularly preferably 1 to 8.

X in the benzene derivative having a long, linear conjugated structure represented by general formula (1) represents a halogen atom such as bromine, chlorine, or iodine.

In the present invention, the benzene derivative having a long, linear conjugated structure represented by general formula (1) is a novel compound. With respect to a conformation, the benzene derivative may be a cis-isomer, a trans-isomer, or a mixture of cis- and trans-isomers.

A process for producing the benzene derivative having a long, linear conjugated structure represented by general formula (1) will be described below.

The process for producing the benzene derivative having a long, linear conjugated structure according to the present invention basically includes a first step and a second step described below.

<First Step>

The first step is a step of producing a pyridine derivative represented by general formula (5), the pyridine derivative being prepared by the reaction shown in reaction formula (1):

reaction formula (1)

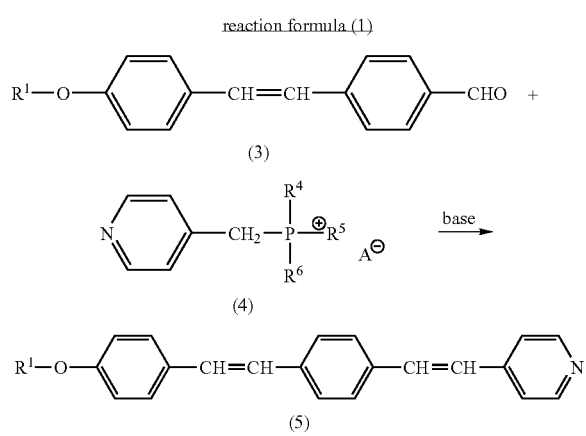

(wherein $R^1$, $R^4$, $R^5$, $R^6$, and A are the same as described above).

The benzaldehyde derivative, which is a first material used in the first step, represented by general formula (3) can be prepared by performing steps A-1 to A-4 according to reaction scheme (2):

reaction scheme (2)

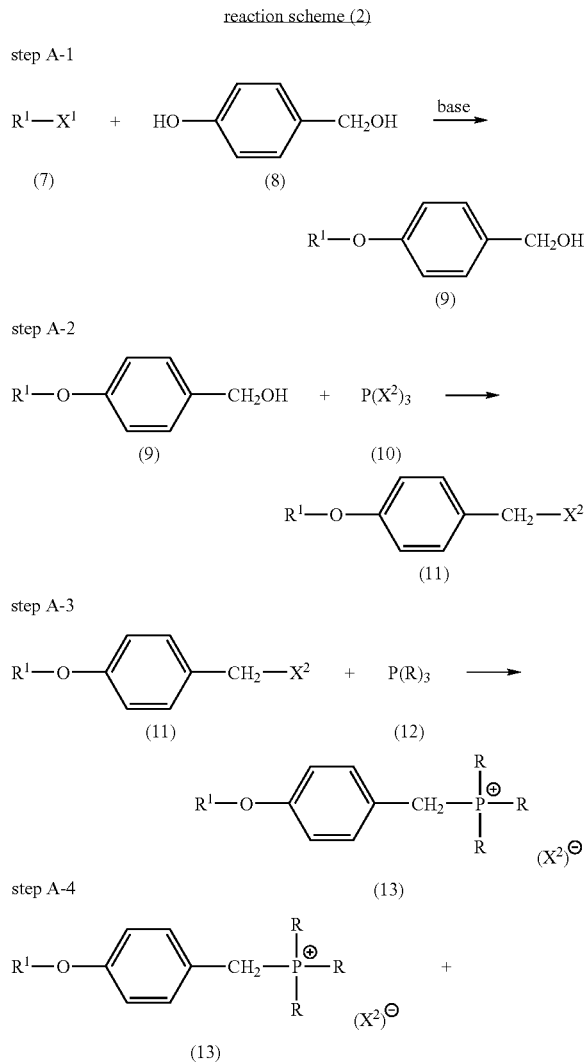

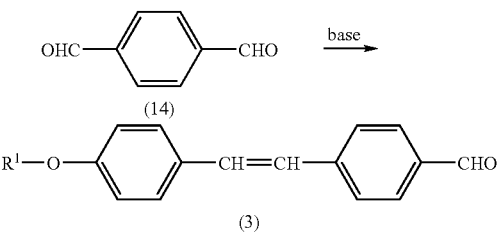

(wherein $R^1$ is the same as above, Rs each represent a monovalent organic group, and $X^1$ and $X^2$ each represent a halogen atom).

Step A-1 is a step of producing a compound represented by general formula (9) by reaction of a halide (compound (7)) with a hydroxybenzyl alcohol (compound (8)) in a solvent in the presence of a base.

$R^1$ in the halide (compound (7)) is a group corresponding to $R^1$ in the benzaldehyde derivative, which is a reaction material used in the first step, represented by general formula (3) and also corresponds to $R^1$ in the benzene derivative having a long, linear conjugated structure represented by general formula (1). $X^1$ represents a halogen atom such as bromine, chlorine, or iodine.

In step A-1, 1 to 3 and preferably 1 to 1.5 moles of the halide (compound (7)) and 1 to 3 and preferably 1 to 1.5 moles of the base, such as sodium hydroxide, potassium hydroxide, sodium ethoxide, or sodium methoxide are used per mole of the hydroxybenzyl alcohol (compound (8)). The reaction is performed in an alcohol solvent, such as methanol or ethanol, at 0° C. to 100° C. and preferably 60° C. to 80° C. for 1 to 20 hours and preferably 5 to 10 hours.

In step A-2, a compound (compound (9)) prepared in step A-1 is allowed to react with a phosphorus halide (compound (10)) in a solvent to prepare a compound represented by general formula (11).

$X^2$ in the phosphorus halide (compound (10)) represents a halogen atom such as bromine, chlorine, or iodine.

In step A-2, 1 to 3 and preferably 1 to 1.5 moles of the phosphorus halide (compound (10)) is used per mole of the compound (compound (9)) prepared in step A-1. The reaction is performed in a solvent, such as ethyl ether, at –30° C. to 60° C. and preferably 0° C. to 30° C. for 1 to 10 hours and preferably 1 to 5 hours.

In step A-3, the compound (compound (11)) prepared in step A-2 is allowed to react with a phosphine compound (compound (12)) in a solvent to prepare a compound represented by general formula (13).

R represents in the phosphine compound (compound (12)) represents a monovalent organic group. The type of R is not limited as long as the compound represented by general formula (11) can be converted into a phosphonium salt. To be specific, for example, a trialkylphosphine, such as triphenylphosphine, trimethylphosphine, or triethylphosphine, may be used.

In step A-3, 1 to 3 and preferably 1 to 1.5 moles of the phosphine compound (compound (12)) is used per mole of the compound (compound (11)) prepared in step A-2. The reaction is performed in a solvent, such as methylene chloride, chloroform, or dichloroethane, at 20° C. to 100° C. and preferably 50° C. to 70° C. for 1 to 10 hours and preferably 3 to 5 hours.

In step A-4, a compound (13) prepared in step A-3 is allowed to react with terephthalaldehyde (compound (14)) in the presence of a base to prepare a benzaldehyde derivative, which is a reaction material used in the first step, represented by general formula (3).

In step A-4, 1 to 3 and preferably 1 to 1.5 moles of terephthalaldehyde (compound (14)) and 1 to 5 and preferably 1 to 3 moles of the base, such as sodium hydroxide, potassium hydroxide, sodium ethoxide, or sodium methoxide, are used per mole of the compound (compound (13)) prepared in A-3. The reaction is performed in an alcohol solvent, e.g., methanol or ethanol −30° C. to 30° C. and preferably −5° C. to 15° C. for 3 to 15 hours and preferably 5 to 10 hours.

In a production process of the present invention, if necessary, after step A-4, the trans-isomer of the benzaldehyde derivative (compound (3)) can be selectively produced by heating the resulting benzaldehyde derivative (compound (3)) in a solvent in the presence of iodine. Subsequently, reaction in the first step can be performed while the trans conformation is maintained. Therefore, the trans-isomer of the benzene derivative represented by general formula (1) can be selectively produced in high yield.

In this case, 0.001 to 0.1 and preferably 0.005 to 0.01 moles of iodine is added per mole of benzaldehyde derivative (compound (3)). The heating temperature is 100° C. to 180° C. and preferably 130° C. to 150° C. Examples of a solvent that can be used include benzene, toluene, o-xylene, m-xylene, p-xylene, chlorobenzene, o-dichlorobenzene, m-dichlorobenzene, and p-dichlorobenzene. These solvent may be used alone or in combination of two or more.

The other reaction material used in the first step, i.e., the phosphonium salt represented by general formula (4) can be prepared, for example, according to reaction formula (3):

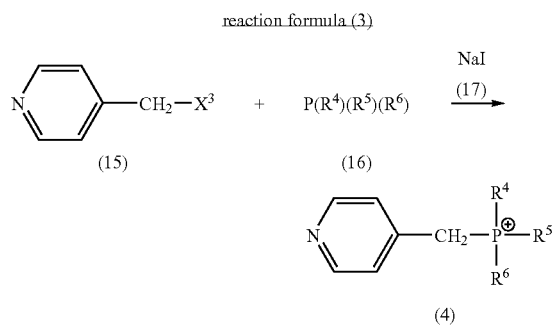

reaction formula (3)

(wherein $R^4$, $R^5$, and $R^6$ are the same as described above, $X^3$ represents a halogen atom).

$X^3$ in the halogenated pyridine compound (compound (15)) represents a halogen atom such as bromine, chlorine, or iodine. $R^4$, $R^5$, and $R^6$ in the phosphine compound (compound (16)) each represent a monovalent organic group. The types of $R^4$, $R^5$, or $R^6$ are not limited as long as the pyridine derivative represented by general formula (15) can be converted into a phosphonium salt. For example, a phenyl group or an alkyl group having 1 to 5 carbon atoms. $R^4$, $R^5$, and $R^6$ may be the same or different. Specific examples of the phosphine compound include triphenylphosphine, trimethylphosphine, and triethylphosphine.

To be specific, 1 to 3 and preferably 1 to 1.5 moles of the phosphine compound (16) and 1 to 3 and preferably 1 to 1.5 moles of sodium iodide (compound (17)) are used per mole of the halogenated pyridine compound (compound (15)). The reaction is performed in a solvent, such as methylene chloride, chloroform, or dichloroethane, at 0° C. to 100° C. and preferably 40° C. to 70° C. for 1 to 10 hours and preferably 1 to 5 hours.

In the first step of the present invention, the benzaldehyde derivative represented by general formula (3) is allowed to react with the phosphonium salt represented by general formula (4) in a solvent in the presence of a base.

Here, 1 to 5 and preferably 1 to 3 moles of the phosphonium salt represented by general formula (4) is added per mole of the benzaldehyde derivative represented by general formula (3).

Examples of the base that can be used in the first step include, but are not limited to, metal hydrides such as sodium hydride; amines such as trimethylamine and triethylamine; alkali hydroxides such as potassium hydroxide and sodium hydroxide; alkoxides such as sodium methoxide, potassium methoxide, sodium ethoxide, and potassium ethoxide; and other compounds such as piperidine, pyridine, potassium cresolate, and alkyllithium. These compounds may be used alone or in combination of two or more.

Here, 1 to 5 and preferably 1 to 3 moles of the base is added per mole of the benzaldehyde derivative represented by general formula (3).

Examples of the reaction solvent include ethers such as dioxane, tetrahydrofuran, and dibutyl ether; nitrites such as acetonitrile and propionitrile; alcohols such as methanol and ethanol; and other compounds such as dimethylformamide, acetone, and water. These may be used alone or in combination of two or more.

With respect to reaction conditions, the reaction temperature is −20° C. to 50° C. and preferably 0° C. to 30° C. The reaction time is 1 to 15 hours and preferably 3 to 10 hours.

After the reaction, if necessary, purification, such as washing or recrystallization, is performed to produce a pyridine derivative represented by general formula (5).

In the production process according to the present invention, before the second step, the trans-isomer of the pyridine derivative (compound (5)) can be selectively produced by heating the resulting pyridine derivative (compound (5)) in a solvent in the presence of iodine. Subsequently, reaction in the second step can be performed while the trans conformation is maintained. Therefore, the trans-isomer of the benzene derivative represented by general formula (1) can be selectively produced in high yield.

In this case, 0.001 to 0.1 and preferably 0.005 to 0.01 moles of iodine is added per mole of the pyridine derivative (compound (5)). The heating temperature is 100° C. to 180° C. and preferably 130° C. to 150° C. Examples of a solvent that can be used include benzene, toluene, o-xylene, m-xylene, p-xylene, chlorobenzene, o-dichlorobenzene, m-dichlorobenzene, and p-dichlorobenzene. These solvents may be used alone or in combination of two or more.

(Second Step)

The second step is a step of producing the benzene derivative having a long, linear conjugated structure represented by general formula (1), the benzene derivative being prepared by the reaction shown in reaction formula (4):

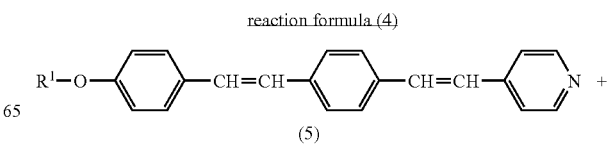

reaction formula (4)

-continued

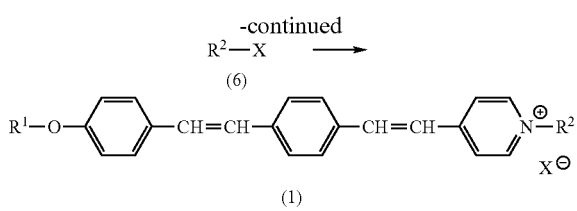

(wherein $R^1$, $R^2$, and X are the same as described above).

$R^2$ and X in the halogenated compound (compound (6)), which is a reaction material used in the second step, correspond to $R^2$ and X, respectively, in the benzene derivative having a long, linear conjugated structure represented by general formula (1). $R^2$ represents an alkyl group or an alkoxy group. The alkyl group has 1 to 18 carbon atoms. Specific examples thereof include a methyl group, an ethyl group, a butyl group, a pentyl group, a hexyl group, an octyl group, a dodecyl group, a pentadecyl group, and an octadecyl group. Among these, an alkyl group having 1 to 8 carbon atoms is particularly preferred. The alkoxy group is represented by general formula: $C_nH_{2n+1}O$, wherein n is preferably 1 to 20 and particularly preferably 1 to 8. X represents a halogen atom such as bromine, chlorine, or iodine.

In the second step, the pyridine derivative represented by general formula (5) is allowed to react with the halogenated compound represented by general formula (6) in a solvent.

Here, 10 to 300 or more and preferably 100 to 200 moles of the halogenated compound represented by general formula (6) is added per mole of the pyridine derivative represented by general formula (5).

Examples of the reaction solvent include methylene chloride, chloroform, and dichloromethane. These may be used alone or in combination of two or more.

With respect to reaction conditions, the reaction temperature is 0° C. to 100° C. and preferably 30° C. to 60° C. The reaction time is 10 to 50 hours and preferably 20 to 40 hours.

After the reaction, if necessary, purification, such as washing or recrystallization, is performed to produce a benzene derivative having a long, linear conjugated structure represented by general formula (1).

The resulting benzene derivative having a long, linear conjugated structure represented by general formula (1) is a novel liquid-crystalline compound.

Next, the liquid-crystal material according to the present invention will be described.

The liquid-crystal material according to the present invention includes the benzene derivative having a long, linear conjugated structure represented by general formula (1) or a compound derived from the benzene derivative having a long, linear conjugated structure.

The term "compound derived from the benzene derivative having a long, linear conjugated structure represented by general formula (1)" (hereinafter, referred to as "polymer") means a homopolymer or copolymer of the benzene derivative; a polymeric compound cross-linked with the benzene derivative using a cross-linking agent; or a polymeric compound prepared by addition reaction of the benzene derivative with a hydrosilyl group-containing polymeric compound, wherein $R^1$ in the benzene derivative having a long, linear conjugated structure represents a group, which is represented by general formula (2), having an unsaturated bond.

Here, the polymer includes at least a repeating unit represented by general formula (18) or (19):

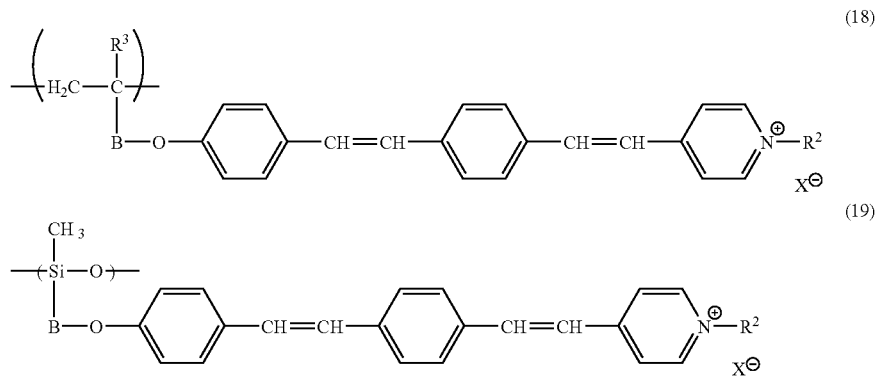

(wherein $R^2$, $R^3$, B, and X are the same as described above).

The polymer may include a repeating unit, which is a copolymer component, derived from, for example, acrylic acid, methacrylic acid, or styrene. When the polymer is a copolymer, the content of the repeating unit represented by general formula (18) or (19) is 50 mole percent or more, preferably 70 mole percent or more, and most preferably 80 mole percent or more.

The number-average molecular weight of the polymer is in the range of 1,000 to tens of millions and preferably tens of thousands to millions.

The polymer can be produced by the following method. For example, in order to produce a homopolymer or copolymer of the benzene derivative represented by general formula (1) or a polymeric compound cross-linked with the benzene derivative using a cross-linking agent, either a predetermined monomer alone or a mixture of a predetermined monomer with a cross-linking agent may be polymerized in the presence of a polymerization initiator by radical polymerization such as solution polymerization, suspension polymerization, emulsion polymerization, or bulk polymerization.

Furthermore, in order to produce a polymeric compound by addition reaction of a hydrosilyl group-containing polymeric compound with the benzene derivative having a long, linear conjugated structure represented by general formula (1), the hydrosilyl group-containing polymeric compound is allowed to react with the benzene derivative having a long, linear conjugated structure represented by general formula (1) in the presence of platonic chloride, a platonic chloride alcohol solution, a complex of platinum and an olefin complex, or a rhodium catalyst such as a rhodium carbonyl complex.

The liquid-crystal material according to the present invention is a material exhibiting smectic liquid crystallinity and including the benzene derivative having a long, linear conjugated structure represented by general formula (1), a composition containing the benzene derivative having a long, linear conjugated structure, the above-described polymer, or a composition containing the polymer.

In the composition containing the benzene derivative having a long, linear conjugated structure represented by general formula (1), the content of the benzene derivative having a long, linear conjugated structure represented by general formula (1) is at least 30 percent by weight or more, preferably 50 percent by weight or more, and most preferably 90 percent by weight or more. Furthermore, the composition exhibits smectic liquid crystallinity due to the liquid-crystalline compound having a long, linear conjugated structure represented by general formula (1).

The other components in the composition are used for adjusting the phase transition temperature of the benzene derivative having a long, linear conjugated structure represented by general formula (1). For example, other liquid-crystalline compounds or other compounds each having a long, linear conjugated structure and having an alkyl group or an alkoxide group at its ends may be used alone or in combination of two or more. The other compounds each having a long, linear conjugated structure and having an alkyl group or an alkoxide group at its ends may be a liquid-crystalline compound or not. These other components may be used alone or in combination of two or more.

The composition containing the benzene derivative having a long, linear conjugated structure represented by general formula (1) can be prepared as follows: the benzene derivative having a long, linear conjugated structure represented by general formula (1) and a predetermined component described above are dissolved in a solvent, and then the solvent is removed by heating, under a reduced pressure, or the like; the benzene derivative having a long, linear conjugated structure represented by general formula (1) and a predetermined component described above are mixed and melted by heating; or sputtering, vacuum evaporation, or the like.

In the composition containing the polymer, the content of the polymer is at least 30 percent by weight or more, preferably 50 percent by weight or more, and most preferably 80 percent by weight or more. Furthermore, the composition exhibits smectic liquid crystallinity due to the liquid-crystalline compound, i.e., the benzene derivative, having a long, linear conjugated structure represented by general formula (1).

The other components in the composition are used for adjusting the phase transition temperature of the polymer. For example, other liquid-crystalline compounds or other compounds each having a long, linear conjugated structure and having an alkyl group or an alkoxide group at its ends may be used alone or in combination of two or more. The other compounds each having a long, linear conjugated structure and having an alkyl group or an alkoxide group at its ends may be a liquid-crystalline compound or not. These other components may be used alone or in combination of two or more.

The composition containing the polymer can be prepared as follows: the polymer and a predetermined component described above are dissolved in a solvent, and then the solvent is removed by heating, under a reduced pressure, or the like; the polymer and a predetermined component described above are mixed and melted by heating; or sputtering, vacuum evaporation, or the like.

The liquid-crystal material according to the present invention can be used as a charge-transport material capable of transporting charge by applying a voltage to the liquid-crystal material in a liquid-crystalline state or in a solid state due to phase transition of the liquid-crystalline state, and can be used for a charge-transport material used in, for example, optical sensors, organic electroluminescent elements (EL elements), photoconductors, spatial modulators, thin-film transistors, charge-transport substances for electrophotographic photoreceptors, photolithographic materials, solar cells, nonlinear optical materials, organic semiconductor capacitors, or other sensors.

EXAMPLES

While the present invention will be described in detail based on examples below, it is understood that the invention is not limited thereto.

Synthetic Example

1. Preparation of Benzaldehyde Derivative Used as Reaction Material Used in First Step Synthetic Example 1-1

Synthesis of 10-bromo-1-decene (Compound (22))

According to reaction formula (5), 10-bromo-1-decene was synthesized.

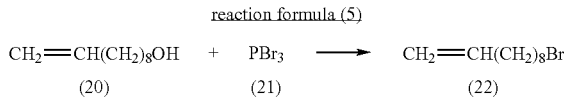

reaction formula (5)

$CH_2\!=\!CH(CH_2)_8OH$ + $PBr_3$ ⟶ $CH_2\!=\!CH(CH_2)_8Br$
(20)  (21)  (22)

First, 24.67 g (0.15 M) of 9-decene-1ol (compound (20)) was dissolved in 180 mL of diethyl ether. The system was purged with nitrogen and cooled in ice. At a solution temperature of 5° C. or less, 2,256 g (0.075 M) of phosphorus tribromide (compound (21)) was added dropwise thereto. After dropwise addition, stirring was performed at 15° C. for 17 hours. The resulting solution was cooled in ice. At a solution temperature of 5° C. or less, 95 mL of methanol was added dropwise. After the dropwise addition, 190 g of a sodium hydrogen carbonate aqueous solution (1 M) was added dropwise, and then stirring was stopped. Next, phase separation was performed. The separated organic layer was washed with 105 g of brine. The resulting organic layer was concentrated and distilled (85° C., 1.8 mmHg) to produce 18.83 g of a target 10-bromo-1-decene (compound (22)) (yield: 57.2%).

<Identification data>

$^1$H-NMR (δ, CDCl$_3$): 1.2-1.5 (m, 10H, —(CH$_2$)$_5$—), 1.8-1.9 (m, 2H, —CH$_2$—), 2.0-2.1 (m, 2H, —CH$_2$—), 3.4 (t, 2H, —CH$_2$Br), 4.9-5.0 (m, 2H, CH$_2$=), 5.7-5.9 (m, 1H, =CH—).

Synthetic Example 1-2

Synthesis of 9-decenoxybenzyl alcohol (Compound (23))

According to reaction formula (6), 9-decenoxybenzyl alcohol (compound (23)) was synthesized.

reaction formula (6)

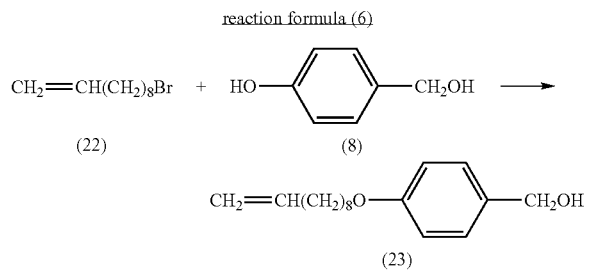

First, 12.80 g (0.10 M) of 4-hydroxybenzyl alcohol (compound (8)) was dissolved in ethanol 190 mL, and 4.0 g (0.10 M) of sodium hydroxide was added thereto. The resulting mixture was heated to 65° C. After heating, 24.14 g (0.11 M) of 10-bromo-1-decene (compound (22)) prepared in Synthetic example 1-1 was added dropwise, and the resulting mixture was aged at a mixture temperature of 76° C. for 6 hours. Next, the generated salt was removed by decantation, and the reaction solution was concentrated. After concentration, the resulting solution was diluted with 350 mL of diethyl ether and washed twice with 100 mL of deionized water. After washing, the organic layer was concentrated to produce crude crystals. The crude crystals were recrystallized twice from 25 mL of hexane. The recrystallized crystals were washed with hexane and dried. Thereby, 16.88 g of 9-decenoxybenzyl alcohol (compound (23)) was produced (yield: 64.3%).

<Identification Data>
$^1$H-NMR ($\delta$, CDCl$_3$): 1.3-1.6 (m, 10H, —(CH$_2$)$_5$—), 1.7-1.8 (m, 2H, —CH$_2$—), 2.0-2.1 (m, 2H, —CH$_2$—), 3.9 (t, 2H, —CH$_2$O—), 4.6 (d, 2H, —CH$_2$OH), 4.9-5.0 (m, 2H, CH$_2$=), 5.7-5.9 (m, 1H, =CH—), 6.8-6.9 (m, 2H, —OPh-), 7.2-7.3 (m, 2H, -PhCH$_2$—). FAB-MASS (Xe): 263 (MH+).

Synthetic Example 1-3

Synthesis of 9-decenoxybenzyl bromide (Compound (24))

According to reaction formula (7), 9-decenoxybenzyl bromide (compound (24)) was synthesized.

reaction formula (7)

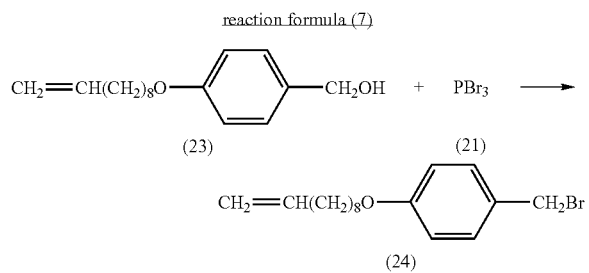

First, 16.05 g (0.061 M) of 9-decenoxybenzyl alcohol (compound (23)) prepared in Synthetic example 1-2 was dissolved in 85 mL of diethyl ether, and the solution was cooled to 0° C. After cooling, 6.76 g (0.022 M) of phosphorus tribromide (compound (21)) was added dropwise thereto at 5° C. or less. The mixture was aged at 5° C. for 2 hours and then at 15° C. for 1.5 hours. After aging, the solution was cooled to 5° C. Then, 38 mL of methanol was added dropwise at 5° C. or less. After dropwise addition, 73.4 g of a sodium hydrogen carbonate aqueous solution (1 M) was added dropwise at 10° C. or less, and then phase separation was performed. After the separation, the separated organic layer was washed with 32 mL of deionized water and then concentrated. Thereby, 18.19 g of 9-decenoxybenzyl bromide (compound (24)) was produced (yield: 91.6%).

<Identification Data>
$^1$H-NMR ($\delta$, CDCl$_3$): 1.3-1.5 (m, 10H, —(CH$_2$)$_5$—), 1.7-1.8 (m, 2H, —CH$_2$—), 2.0-2.1 (m, 2H, —CH$_2$—), 3.9 (t, 2H, —CH$_2$O—), 4.5 (s, 2H, —CH$_2$Br), 4.9-5.0 (m, 2H, CH$_2$=), 5.7-5.9 (m, 1H, =CH—), 6.8-6.9 (m, 2H, —OPh-), 7.2-7.3 (m, 2H, -PhCH$_2$—), FAB-MASS (Xe): 325 (M+).

Synthetic Example 1-4

Synthesis of 9-decenoxybenzyltriphenylphosphonium bromide (Compound (26))

According to reaction formula (8), 9-decenoxybenzyltriphenylphosphonium bromide (compound (26)) was synthesized.

reaction formula (8)

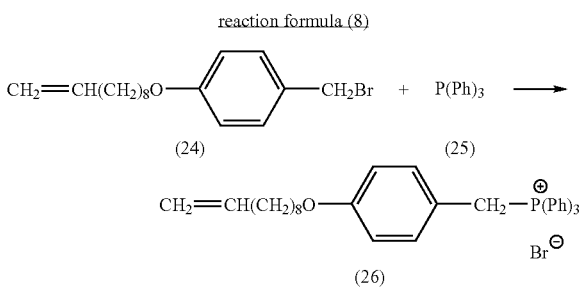

First, 17.23 g (0.053 M) of 9-decenoxybenzyl bromide (compound (24)) prepared in Synthetic example 1-3 and 13.92 g (0.053M) of triphenylphosphine (compound (25)) were added to 53 mL of chloroform. The resulting mixture was heated to 60° C. and then aged for 1.5 hours. After aging, the resulting reaction mixture was concentrated to produce crude crystals. The resulting crude crystals were washed with diethyl ether, filtrated, and dried. Thereby, 29.19 g of 9-decenoxybenzyltriphenylphosphonium bromide (compound (26)) was produced (yield: 93.7%).

<Identification Data>
$^1$H-NMR ($\delta$, CDCl$_3$): 1.3-1.5 (m, 10H, —(CH$_2$)$_5$—), 1.7-1.8 (m, 2H, —CH$_2$—), 2.0-2.1 (m, 2H, —CH$_2$—), 3.8 (t, 2H, —CH$_2$O—), 4.9-5.0 (m, 2H, —CH$_2$=), 5.2 (d, 2H, —CH$_2$P—), 5.7-5.9 (m, 1H, =CH—), 5.2 (d, 2H, —CH$_2$P—), 6.6 (d, 2H, —OPh-), 7.0 (dd, 2H, -PhCH$_2$—), 7.6-7.8 (m, 15H, (Ph)$_3$). $^{31}$P-NMR ($\delta$, CDCl$_3$): 28.0 ppm. FAB-MASS (Xe): 507 (M–Br).

Synthetic Example 1-5

Synthesis of 9-decenoxystilbene aldehyde (Compound (27))

According to reaction formula (9), 9-decenoxystilbene aldehyde (compound (27)) was synthesized.

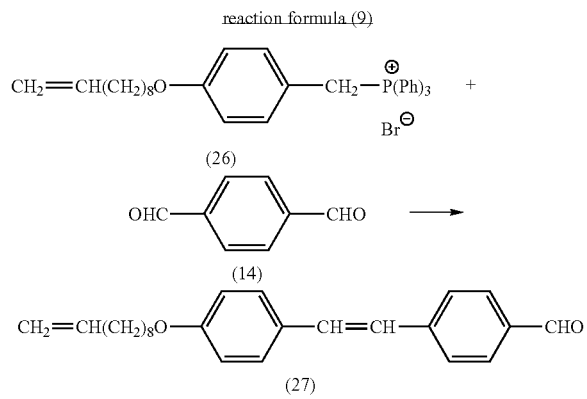

First, 23.07 g (0.039 M) of 9-decenoxybenzyltriphenylphosphonium bromide (compound (26)) prepared in Synthetic example 1-4 and 5.91 g of terephthalaldehyde (compound (14)) were dissolved in 315 mL of ethanol. The resulting solution was cooled to −2° C., and then 25.64 g of a sodium ethoxide ethanol solution (21 percent by weight, aldrich) was added dropwise at 0° C. or less. Aging was performed at a mixture temperature of 0° C. or less for 1.5 hours and then at a mixture temperature of 10° C. to 15° C. for 2 hours. After aging, 39 g of deionized water was added dropwise. Then, the precipitated crystals were filtrated and washed with 50 mL of 60% aqueous ethanol and 30 mL of ethanol, followed by drying. Thereby, 7.12 g of 9-decenoxystilbene aldehyde (compound (27)) was produced (yield: 50.0%).

<Identification Data>
$^1$H-NMR (δ, CDCl$_3$): 1.3-1.5 (m, 10H, —(CH$_2$)$_5$—), 1.7-1.8 (m, 2H, —CH$_2$—), 2.0-2.1 (m, 2H, —CH$_2$—), 3.9-4.0 (m, 2H, —CH$_2$O—), 4.9-5.0 (m, 2H, CH$_2$=), 5.7-5.9 (m, 1H, =CH—), 6.5-7.9 (m, 10H, Ph, —CH=CH—). FAB-MASS (Xe): 363 (MH+).

Subsequently, 14 mL of p-xylene and 8.2 mg iodine were added to 4.34 g (0.012 M) of 9-decenoxystilbene aldehyde (compound (27)). The resulting mixture was heated to 140° C. and aged for 4 hours. After aging, the mixture was cooled to room temperature. The precipitated crystals were filtrated and washed with 25 mL of ethanol, followed by drying. Then, 88 mL of chloroform was added to the resulting crystals, followed by stirring at room temperature for 20 minutes. After stirring, insoluble matter was removed by filtration, and then the filtrate was concentrate. Thereby, the trans-isomer of 2.35 g of 9-decenoxystilbene aldehyde (compound (27)) was produced (yield: 54.1%).

<Identification Data>
$^1$H-NMR (δ, CDCl$_3$): 1.3-1.5 (m, 10H, —(CH$_2$)$_5$—), 1.7-1.8 (m, 2H, —CH$_2$—), 2.0-2.1 (m, 2H, —CH$_2$—), 3.9 (t, 2H, —CH$_2$O—), 4.9-5.0 (m, 2H, CH$_2$=), 5.7-5.9 (m, 1H, =CH—), 6.9 (d, 2H, —OPh-), 7.0 (d, 1H, —CH=CH—), 7.2 (d, 1H, —CH=CH—), 7.5 (d, 2H, Ph), 7.6 (d, 2H, Ph), 7.8 (d, 2H, Ph). FAB-MASS (Xe): 363 (MH+).

2. Preparation of Phosphonium Salt Used as Reaction Material Used in First Step

Synthetic Example 2-1

Synthesis of 4-chloromethylpyridine (Compound (30))

According to reaction formula (10), 4-chloromethylpyridine (compound (30)) was synthesized.

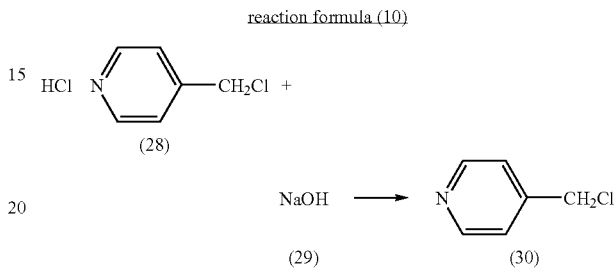

First, 10.19 g (0.06 M) of 4-chloromethylpyridine hydrochloride (compound (28)) was dissolved in 29.91 g of deionized water, and 20.60 g of 12% sodium hydroxide (compound (29)) aqueous solution was added dropwise thereto. After dropwise addition, 60.15 g of dichloromethane was added, and phase separation was performed. The separated organic layer was concentrated to produce 7.52 g of 4-chloromethylpyridine (compound (30)) (yield: 98.0%).

<Identification Data>
$^1$H-NMR (δ, CDCl$_3$): 4.5 (s, 2H, CH$_2$Cl), 7.31-7.34 (m, 2H, Py), 8.61-8.67 (m, 2H, Py).

Synthetic Example 2-2

Synthesis of Pyridinium Methyltriphenylphosphonium Iodide (Compound (31))

According to reaction formula (11), pyridinium methyltriphenylphosphonium iodide (compound (31)) was synthesized.

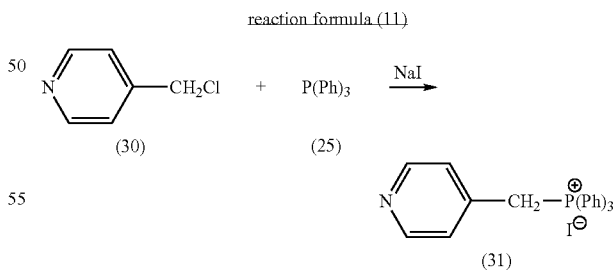

First, 7.97 g (0.06 M) of 4-chloromethylpyridine (compound (30)) prepared in Synthetic example 2-1 and 15.77 g (0.06 M) of triphenylphosphine (compound (25)) were dissolved in 97.81 g of chloroform. Then, 48.57 g of a solution prepared by dissolving 9.11 g (0.06 M) of sodium iodide in deionized water was added thereto. The resulting mixture was heated to 70° C. and aged for 2 hours. After aging, the reaction mixture was subjected to phase separation. After the separated organic layer was concentrated, the precipitated crystals were filtrated and washed with 36.11 g of chloroform, followed by drying. Thereby, 15.80 g of pyridinium methyltriphenylphosphonium iodide (compound (31)) was produced (yield: 54.5%).

<Identification Data>
$^1$H-NMR ($\delta$, DMSO$_3$): 5.25 (d, 2H, CH$_2$P), 6.95-6.98 (m, 2H, Py), 7.68-7.80 (m, 12H, Ph), 7.87-7.96 (m, 3H, Ph), 8.41-8.43 (m, 2H; Py). FAB-MASS (Xe): 355 (M–1).

Example 1

<First Step>

Synthesis of Trans-isomer of Pyridine Derivative (Compound (33))

According to reaction formula (12), a pyridine derivative (compound (33)) was synthesized.

1.64 g of crude crystals of a pyridine derivative (compound (33)) was produced (yield: 85.1%).

<Identification Data>

FAB-MASS (Xe): 438 (MH+).

Subsequently, 1.64 g (0.00374 M) of the resulting crude crystals of the pyridine derivative (compound (33)) and 2.5 mg of iodine were added to 11.5 g of p-xylene. The resulting mixture was heated with a bath having a temperature of 150° C. and aged for 4 hours. Then, the mixture was cooled to room temperature, and the precipitated crystals were washed with ethanol. Thereby, 0.73 g of the trans-isomer of the pyridine derivative (compound (33)) was produced (yield: 45.1%).

<Identification Data>

$^1$H-NMR ($\delta$, CDCl$_3$): 1.20-1.50 (m, 10H, —(CH$_2$)$_5$—), 1.76-1.82 (m, 2H, —CH$_2$—), 2.00-2.20 (m, 2H, —CH$_2$—), reaction formula (12)

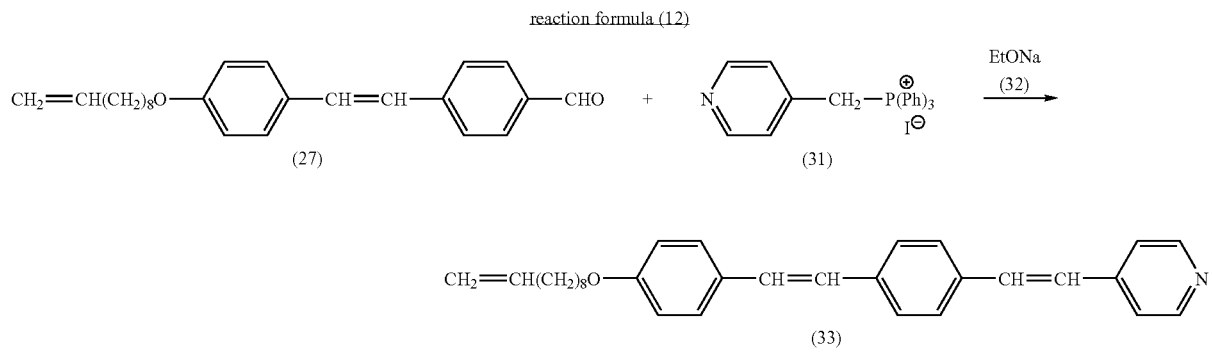

First, 3.18 g (0.0044 M) of pyridinium methyltriphenylphosphonium iodide (compound (31)) prepared in Synthetic example 2-2 was dissolved in 22.40 g of methanol, and 4.29 g of a sodium ethoxide (compound (32)) ethanol solution (21 percent by weight, aldrich) was added dropwise thereto. Then, 22.53 g of chloroform containing 1.59 g of 9-decenoxystilbene aldehyde (compound (27)) prepared in Synthetic example 1-5 was added dropwise at room temperature. After dropwise addition, the reaction mixture was aged at room temperature for 3 hours and then concentrated. After concentration, the resulting crude crystals were washed with 19.61 g of methanol and then filtrated, followed by drying. Thereby, 3.98 (t, 2H, —CH$_2$O—), 4.92-5.01 (m, 2H, CH$_2$=), 5.75-5.88 (m, 1H, =CH—), 6.82-6.93 (d, 2H, Ph), 6.95 (d, 1H, —CH=), 7.02 (d, 1H, —CH=), 7.11 (d, 1H, —CH=), 7.30 (d, 1H, —CH=), 7.35-7.38 (m, 2H, Py), 7.42-7.57 (m, 6H, Ph), 8.55-8.60 (m, 2H, Py). FAB-MASS (Xe): 438 (MH+).

<Second Step>

Synthesis of Trans-isomer of Benzene Derivative (Compound (35))

According to reaction formula (13), a benzene derivative (compound (35)) was synthesized.

reaction formula (13)

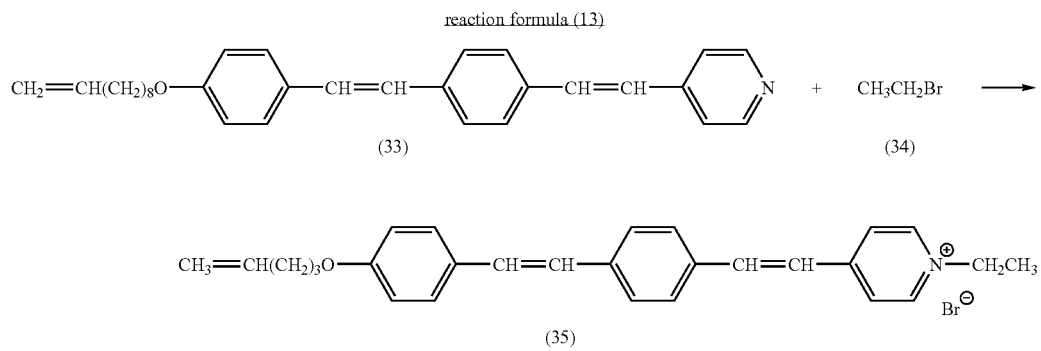

First, 1.18 g (0.0027 M) of the trans-isomer of the pyridine derivative (compound (33)) prepared in the first step and 60.77 g of ethyl bromide (compound (34)) were added to 59.11 g of chloroform, and the resulting mixture was stirred under heating at 40° C. for 40 hours. After aging, the reaction mixture was concentrated to produce crude crystals. Then, 27.33 g of acetone was added to the resulting crude crystals. The resulting mixture was heated to 60° C. and filtrated under heating. Thereby, 1.04 g of the target benzene derivative (compound (35)) was produced (yield: 70.7%).

<Identification Data>

$^1$H-NMR (δ, CDCl$_3$): 1.26-1.50 (m, 10H, —(CH$_2$)$_5$—), 1.70 (t, 3H, —CH$_3$), 1.76-1.82 (m, 2H, —CH$_2$—), 2.00-2.20 (m, 2H, —CH$_2$—), 3.97 (t, 2H, —CH$_2$O—), 4.88 (ddd, 2H, —CH$_2$—), 4.90-5.03 (m, 2H, —CH$_2$=), 5.75-5.88 (m, 1H, =CH—), 6.90 (d, 2H, —OPh-), 6.95 (d, 1H, —CH=), 7.11 (d, 1H, —CH=), 7.16 (d, 1H, —CH=), 7.45 (d, 2H, —OPh-), 7.52 (d, 2H, -Ph-), 7.60 (d, 2H, -Ph-), 7.67 (d, 1H, —CH=), 8.01 (d, 2H, Py), 9.17 (d, 2H, Py). FAB-MASS (Xe): 467 (M−Br).

IR (KBr, cm−1): 3,022 (aromatic C—H stretching vibration), 2,924-2,853 (aliphatic C—H stretching vibration), 1,642 (C=C stretching vibration), 1,590-1,467 (C=C, C=N skeletal vibration), 1,253 (C—O—C antisymmetric stretching vibration), 966 (—C=C— out-of-plane deformation vibration), 839 (aromatic C—H in-plane deformation vibration).

In addition, the gap between two glass substrates was filled with the resulting benzene derivative (compound (35)) and heated to a temperature exceeding the liquid crystal-isotropic liquid transition temperature. Light transmitted through the benzene derivative was observed with a polarizing microscope. The observation indicated that the benzene derivative was a liquid-crystalline compound exhibiting a smectic phase oriented perpendicularly to the substrates.

INDUSTRIAL APPLICABILITY

As has been described above, an inventive benzene derivative having a long, linear conjugated structure represented by general formula (1) is a novel compound. The benzene derivative having a long, linear conjugated structure is a compound having smectic liquid crystallinity. A liquid-crystal material containing the benzene derivative having a long, linear conjugated structure or a compound derived from the derivative can be used as a charge-transport material capable of transporting charge by applying a voltage to the liquid-crystal material in a liquid-crystalline state or in a solid state due to phase transition of the liquid-crystalline state, and can be used for a charge-transport material used in, for example, optical sensors, organic electroluminescent elements (EL elements), photoconductors, spatial modulators, thin-film transistors, charge-transport substances for electrophotographic photoreceptors, photolithographic materials, solar cells, nonlinear optical materials, organic semiconductor capacitors, or other sensors.

The invention claimed is:

1. A liquid crystal benzene derivative having a long, linear conjugated structure represented by general formula (1):

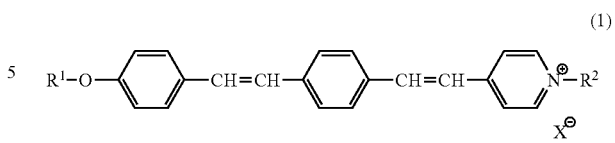

wherein R$^1$ represents a straight or branched alkyl group having 6 to 18 carbon atoms, an alkoxy group having 6 to 18 carbon atoms, or a group having an unsaturated bond represented by general formula (2):

(wherein R$^3$ represents a hydrogen atom or a methyl group, and B represents an alkylene group, —CO—O—(CH$_2$)n, —C$_6$H$_4$—CH$_2$—, or —CO—), R$^2$ represents an alkyl group or an alkoxy group, and X represents a halogen atom.

2. A process for producing a benzene derivative having a long, linear conjugated structure represented by general formula (1):

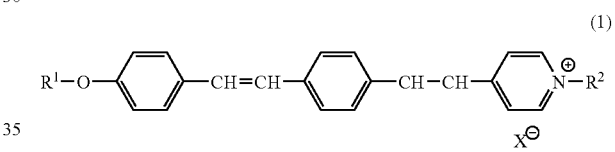

wherein R$^1$ represents a straight or branched alkyl group having 6 to 18 carbon atoms, an alkoxy group having 6 to 18 carbon atoms, or a group having an unsaturated bond represented by general formula (2):

(wherein R$^3$ represents a hydrogen atom or a methyl group, and B represents an alkylene group, —CO—O—(CH$_2$)n, —C$_6$H$_4$—CH$_2$—, or —CO—), R$^2$ represents an alkyl group or an alkoxy group, and X represents a halogen atom, the process comprising: a first step of allowing a benzaldehyde derivative represented by general formula (3):

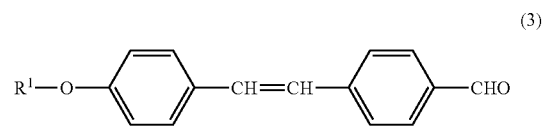

(wherein R$^1$ the same as defined in general formula (1) above);

to react with a phosphonium salt represented by (4):

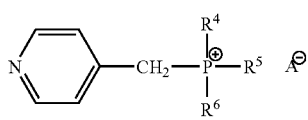 (4)

(wherein $R^4$, $R^5$ and $R^6$ are each a monovalent organic group, and A represents a halogen atom), in the presence of a base to produce a pyridine derivative represented by general formula (5):

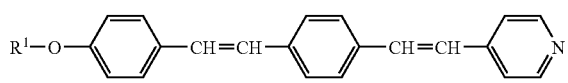 (5)

(wherein $R^1$ is the same as described in general formula (1) above); and a second, step of allowing the pyridine derivative to react with a halogenated compound represented by general formula (6):

 (6)

(wherein $R^2$ and X are the same as described in general formula (1) above).

3. A liquid-crystal material comprising: a liquid crystal benzene derivative having a long, linear conjugated structure represented by general formula (1):

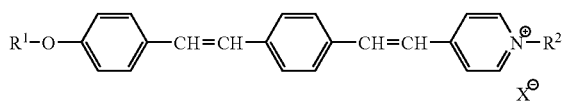 (1)

wherein $R^1$ represents a straight or branched alkyl group having 6 to 18 carbon atoms, an alkoxy group having 6 to 18 carbon atoms, or a group having an unsaturated bond represented by general formula (2):

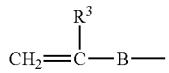 (2)

(wherein $R^3$ represents a hydrogen atom or a methyl group, and B represents an alkylene group, —CO—O—$(CH_2)n$, —$C_6H_4$—$CH_2$—, or —CO—), $R^2$ represents an alkyl group or an alkoxy group, and X represents a halogen atom.

* * * * *